(12) United States Patent
Ting (10) Patent No.: US 11,666,302 B2
(45) Date of Patent: Jun. 6, 2023

(54) ONE-PIECE DIAPHRAGM AND RING FOR STETHOSCOPE CHESTPIECE

(71) Applicant: MDF Instruments USA LLC, Rincon, PR (US)

(72) Inventor: Darren Talun Chiao Ting, Rincon, PR (US)

(73) Assignee: MDF Instruments USA LLC, Rincon, PR (US)

( * ) Notice: Subject to any disclaimer, the term of this patent is extended or adjusted under 35 U.S.C. 154(b) by 319 days.

(21) Appl. No.: 16/988,651

(22) Filed: Aug. 8, 2020

(65) Prior Publication Data

US 2021/0038183 A1 Feb. 11, 2021

Related U.S. Application Data

(60) Provisional application No. 62/884,606, filed on Aug. 8, 2019.

(51) Int. Cl.
*A61B 7/02* (2006.01)
*G10K 13/00* (2006.01)
(52) U.S. Cl.
CPC ............... *A61B 7/02* (2013.01); *G10K 13/00* (2013.01)

(58) Field of Classification Search
CPC .................................. A61B 7/02; G10K 13/00
See application file for complete search history.

(56) References Cited

U.S. PATENT DOCUMENTS

| | | | | |
|---|---|---|---|---|
| 6,019,187 A | * | 2/2000 | Appavu | A61B 7/02 181/131 |
| 6,520,281 B1 | * | 2/2003 | Deslauriers | A61B 7/02 600/528 |
| 8,939,251 B2 | | 1/2015 | Ting | |
| D724,206 S | | 3/2015 | Ting | |
| D724,728 S | | 3/2015 | Ting | |
| 9,486,180 B2 | | 11/2016 | Ting | |
| 2014/0005574 A1 | | 1/2014 | Ting | |
| 2015/0129350 A1 | | 5/2015 | Ting | |
| 2018/0344282 A1 | * | 12/2018 | Lin | A61B 7/02 |
| 2020/0187894 A1 | * | 6/2020 | Lin | A61B 7/02 |

* cited by examiner

*Primary Examiner* — Jeremy A Luks
(74) *Attorney, Agent, or Firm* — The Law Office of Patrick F. O'Reilly III, LLC (57) ABSTRACT

A one-piece diaphragm and ring for a stethoscope chestpiece is disclosed herein. The one-piece diaphragm and ring includes a diaphragm portion having a flat disk shape; and a ring portion connected to an outer periphery of the diaphragm portion, the ring portion being integrally formed with the diaphragm portion, and the ring portion configured to be attached to a rim of a chestpiece body portion. A chestpiece of a stethoscope that includes the one-piece diaphragm and ring is also disclosed herein.

24 Claims, 7 Drawing Sheets

ONE-PIECE DIAPHRAGM AND RING FOR STETHOSCOPE CHESTPIECE

CROSS-REFERENCE TO RELATED APPLICATIONS

This patent application claims priority to, and incorporates by reference in its entirety, U.S. Provisional Patent Application No. 62/884,606, entitled "One-Piece Diaphragm And Ring For Stethoscope Chestpiece", filed on Aug. 8, 2019.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a one-piece diaphragm and ring for a stethoscope chestpiece. More particularly, the invention relates to a one-piece diaphragm and ring for a stethoscope chestpiece that comprises integrally formed diaphragm and ring portions.

2. Background

It is known in the art that a medical practitioner employs various devices during the course of examination of a patient. One such instrument is a stethoscope that is used by physicians, nurses, and paramedics in the early stage of any general examination and/or proper vital sign examination of a patient.

A stethoscope is an acoustic medical device for auscultation, or listening to the internal sounds of a body. It is often used to listen to heart sounds. It is also used to listen to intestines and blood flow in arteries and veins. Acoustic stethoscopes operate on the transmission of sounds from the chestpiece, via air-filled hollow tubes, to a binaural (headset) that a practitioner uses to listen to the acoustic sounds of a patient. The chestpiece usually consists of a diaphragm and a housing that supports the diaphragm within the chestpiece body. When the diaphragm is placed on the patient, body sounds vibrate the diaphragm, creating acoustic pressure waves which travel up the tubing to the binaural and the listener's ears.

The proper operation of a stethoscope is essential, since a practitioner, nurse or a doctor, uses a stethoscope to listen to the sounds of a patient's body to determine normal functioning and abnormalities.

The chestpiece of a conventional stethoscope typically contains a separate chill ring and diaphragm attached to a metallic chestpiece body portion. In conventional stethoscopes, the two-piece construction of the chill ring and diaphragm often results in increased sound leakage from the stethoscope. This increased sound leakage deleteriously reduces the effectiveness of the stethoscope for auscultation.

Therefore, what is needed is a one-piece diaphragm and ring for a stethoscope that reduces sound leakage as compared to conventional stethoscope chestpieces with separate diaphragms and chill rings. Moreover, a one-piece diaphragm and ring for a stethoscope is needed that is particularly useful for high frequency sounds. Furthermore, what is needed is a one-piece diaphragm and ring for a stethoscope that is able to be formed from a polymeric material that is non-toxic, odorless, and pliable.

BRIEF SUMMARY OF EMBODIMENTS OF THE INVENTION

Accordingly, the present invention is directed to a one-piece diaphragm and ring for a stethoscope chestpiece that substantially obviates one or more problems resulting from the limitations and deficiencies of the related art.

In accordance with one or more embodiments of the present invention, there is provided a one-piece diaphragm and ring for a stethoscope chestpiece. The one-piece diaphragm and ring includes a diaphragm portion having a flat disk shape; and a ring portion connected to an outer periphery of the diaphragm portion, the ring portion being integrally formed with the diaphragm portion, and the ring portion configured to be attached to a rim of a chestpiece body portion.

In a further embodiment of the present invention, the diaphragm portion and the ring portion are formed from silicone.

In yet a further embodiment, the silicone forming the diaphragm portion and the ring portion has a density of approximately 1.15 grams per cubic centimeter.

In still a further embodiment, the silicone forming the diaphragm portion and the ring portion has an elasticity between approximately 7 megapascals and approximately 8 megapascals, inclusive.

In yet a further embodiment, in a low frequency range between 100 Hertz and 500 Hertz, the one-piece diaphragm and ring is configured to result in a sound loss reduction of approximately 3.5 decibels as compared to a conventional two-piece diaphragm and ring formed from polyvinyl chloride.

In still a further embodiment, in a high frequency range between 500 Hertz and 1,000 Hertz, the one-piece diaphragm and ring is configured to result in a sound loss reduction of approximately 3.0 decibels as compared to a conventional two-piece diaphragm and ring formed from polyvinyl chloride.

In yet a further embodiment, the diaphragm portion has a thickness between approximately 0.27 millimeters and approximately 0.30 millimeters, inclusive, in an unstretched state prior to being installed on the chestpiece body portion of the stethoscope chestpiece.

In still a further embodiment, the diaphragm portion has a thickness between approximately 0.25 millimeters and approximately 0.28 millimeters, inclusive, in a stretched state after being installed on the chestpiece body portion of the stethoscope chestpiece.

In yet a further embodiment, the ring portion is configured to overlap the rim of the chestpiece body portion by approximately 5 millimeters to 6 millimeters, inclusive, after being installed on the chestpiece body portion of the stethoscope chestpiece.

In accordance with one or more other embodiments of the present invention, there is provided a chestpiece of a stethoscope that includes a chestpiece body portion having a first end and a second end, the second end being oppositely disposed with respect to the first end, the second end of the chestpiece body portion having a rim; and a one-piece diaphragm and ring attached to the chestpiece body portion. The one-piece diaphragm and ring includes a diaphragm portion having a flat disk shape; and a ring portion connected to an outer periphery of the diaphragm portion, the ring portion being integrally formed with the diaphragm portion, and the ring portion attached to the rim at the second end of the chestpiece body portion.

In a further embodiment of the present invention, the chestpiece body portion comprises an annular projection extending outwardly from a peripheral side thereof, and wherein the ring portion of the one-piece diaphragm and ring comprises a circumferential internal groove disposed therein, the annular projection of the chestpiece body portion configured to matingly engage with said circumferential internal groove of the ring portion of the one-piece diaphragm and ring.

In yet a further embodiment, the circumferential internal groove of the ring portion of the one-piece diaphragm and ring has an inner diameter that is smaller than an outer diameter of the annular projection of the chestpiece body portion so that the diaphragm portion of the one-piece diaphragm and ring stretches when the one-piece diaphragm and ring is attached to the chestpiece body portion.

In still a further embodiment, the diaphragm portion and the ring portion of the one-piece diaphragm and ring are formed from silicone.

In yet a further embodiment, the silicone forming the diaphragm portion and the ring portion has a density of approximately 1.15 grams per cubic centimeter.

In still a further embodiment, the silicone forming the diaphragm portion and the ring portion has an elasticity between approximately 7 megapascals and approximately 8 megapascals, inclusive.

In yet a further embodiment, in a low frequency range between 100 Hertz and 500 Hertz, the one-piece diaphragm and ring is configured to result in a sound loss reduction of approximately 3.5 decibels as compared to a conventional two-piece diaphragm and ring formed from polyvinyl chloride.

In still a further embodiment, in a high frequency range between 500 Hertz and 1,000 Hertz, the one-piece diaphragm and ring is configured to result in a sound loss reduction of approximately 3.0 decibels as compared to a conventional two-piece diaphragm and ring formed from polyvinyl chloride.

In yet a further embodiment, the diaphragm portion of the one-piece diaphragm and ring has a thickness between approximately 0.27 millimeters and approximately 0.30 millimeters, inclusive, in an unstretched state prior to being installed on the chestpiece body portion of the stethoscope chestpiece.

In still a further embodiment, the diaphragm portion of the one-piece diaphragm and ring has a thickness between approximately 0.25 millimeters and approximately 0.28 millimeters, inclusive, in a stretched state after being installed on the chestpiece body portion of the stethoscope chestpiece.

In yet a further embodiment, the ring portion of the one-piece diaphragm and ring is configured to overlap the rim of the chestpiece body portion by approximately 5 millimeters to 6 millimeters, inclusive.

In still a further embodiment, the one-piece diaphragm and ring is configured to be a single-use diaphragm and ring that is discarded after being used with a patient.

In yet a further embodiment, a peripheral side of the ring portion of the one-piece diaphragm and ring has a thickness that is substantially greater than the remainder of the one-piece diaphragm and ring so that the peripheral side of the ring portion is capable of absorbing an impact without fracturing.

In still a further embodiment, the diaphragm portion and the ring portion of the one-piece diaphragm and ring are formed from a flexible material so that the one-piece diaphragm and ring is capable of conforming to one or more contours of a body portion of a patient.

In yet a further embodiment, the diaphragm portion and the ring portion of the one-piece diaphragm and ring are formed from a flexible material that enables the one-piece diaphragm and ring to be quickly and easily removed from, and installed on the chestpiece body portion so that the one-piece diaphragm and ring is readily interchangeable.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
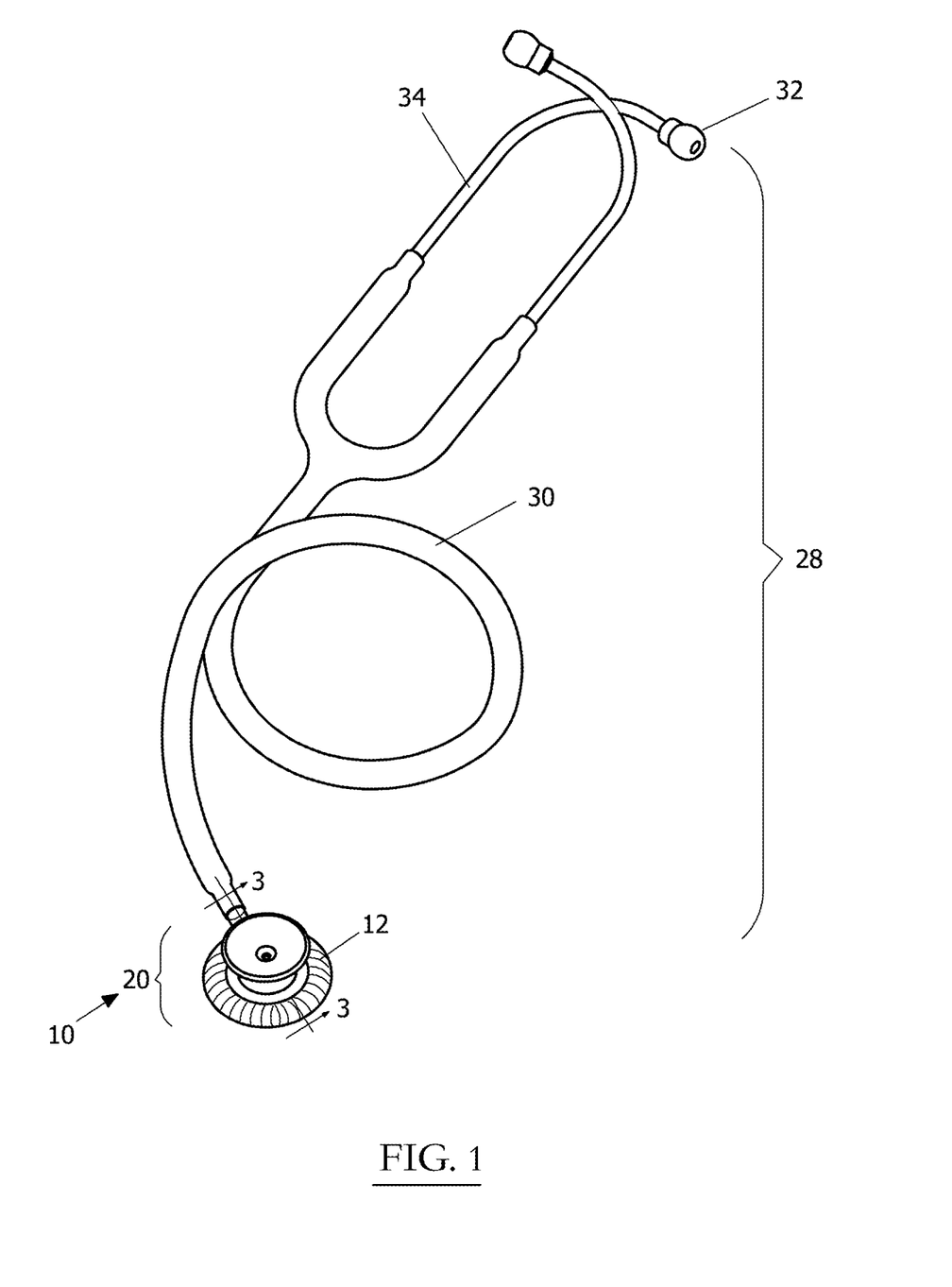
FIG. 1 is a perspective view of a stethoscope with a chestpiece having a one-piece diaphragm and ring, according to an illustrative embodiment of the invention.

An illustrative embodiment of a stethoscope with a chestpiece having a one-piece diaphragm and ring is seen generally at 10 in FIG. 1. As shown in FIG. 1, the stethoscope 10 generally comprises a chestpiece 20 and a binaural assembly 28 that includes two earpieces 32. Also, as illustrated in FIG. 1, the binaural assembly 28 of the stethoscope 10 includes an acoustic tube 30 that is acoustically coupled to a headset with two (2) ear tubes 34. Each of the ear tubes 34 is provided with a respective earpiece 32 disposed on the end thereof. In addition, as shown in FIG. 1, the chestpiece 20 of the stethoscope 10 is provided with a one-piece diaphragm and ring 12 fitted thereon.

Now, with collective reference to FIGS. 3 and 4, the illustrative embodiment of the chestpiece 20 of the stethoscope 10 will be described. Initially, as shown in these two figures, it can be seen that the stethoscope chestpiece 20 generally includes a chestpiece body portion 26 having a first end and a second end, a frustoconical bell portion 22 at the first end of the chestpiece body portion 26, a one-piece diaphragm and ring 12 attached to the second end of the chestpiece body portion 26, and a rotatable acoustic valve 40 rotatably disposed in an elongate recess of the chestpiece body portion 26. In the illustrative embodiment, the rotatable acoustic valve 40 is selectively positionable between a first operative position (e.g., in which sounds are transmitted from one-piece diaphragm and ring 12 to the user of the stethoscope) and a second operative position (e.g., in which sounds are transmitted from the frustoconical bell portion 22 to the user of the stethoscope).

Figure 3:
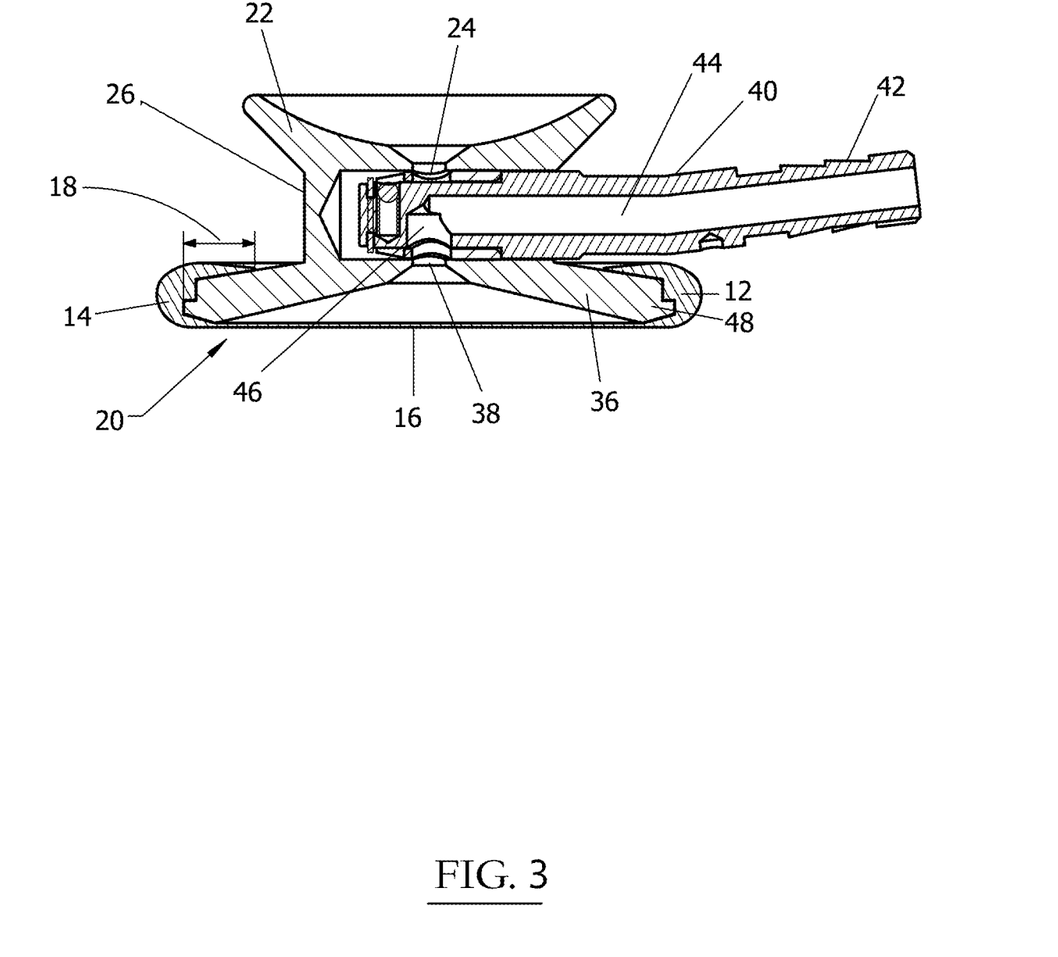
FIG. 3 is a cross-sectional view of the stethoscope chestpiece of FIG. 2, which is cut along the cutting-plane line 3-3 extending transversely through the center of the stethoscope chestpiece in FIG. 1.
Figure 4:
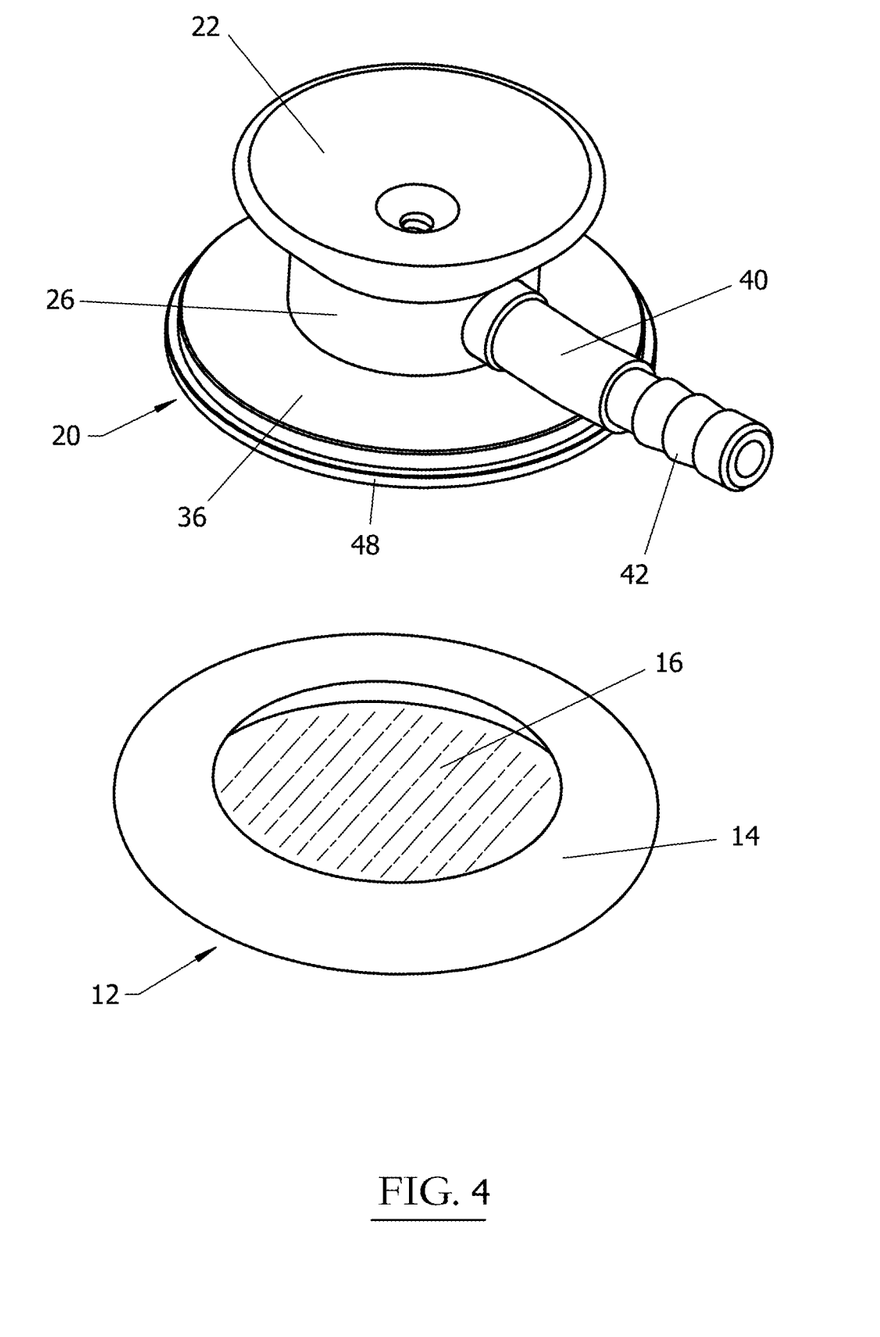
FIG. 4 is an exploded perspective view of the stethoscope chestpiece of the stethoscope of FIG. 1, wherein the one-piece diaphragm and ring is shown exploded from the chestpiece body portion.

As illustrated in the transverse sectional view of FIG. 3, the rotatable acoustic valve 40 includes a longitudinal acoustic passageway portion 44 extending along a length thereof and a transverse acoustic passageway portion 46 extending generally perpendicular to the longitudinal acoustic passageway portion 44. In these figures, it can be seen that the longitudinal acoustic passageway portion 44 is fluidly coupled to the transverse acoustic passageway portion 46 so that sounds received from the selected one of the one-piece diaphragm and ring 12 and the frustoconical bell portion 22 of the stethoscope chestpiece 20 can be transmitted through the rotatable acoustic valve 40 to the binaural assembly 28 of the stethoscope 10.

Figure 2:
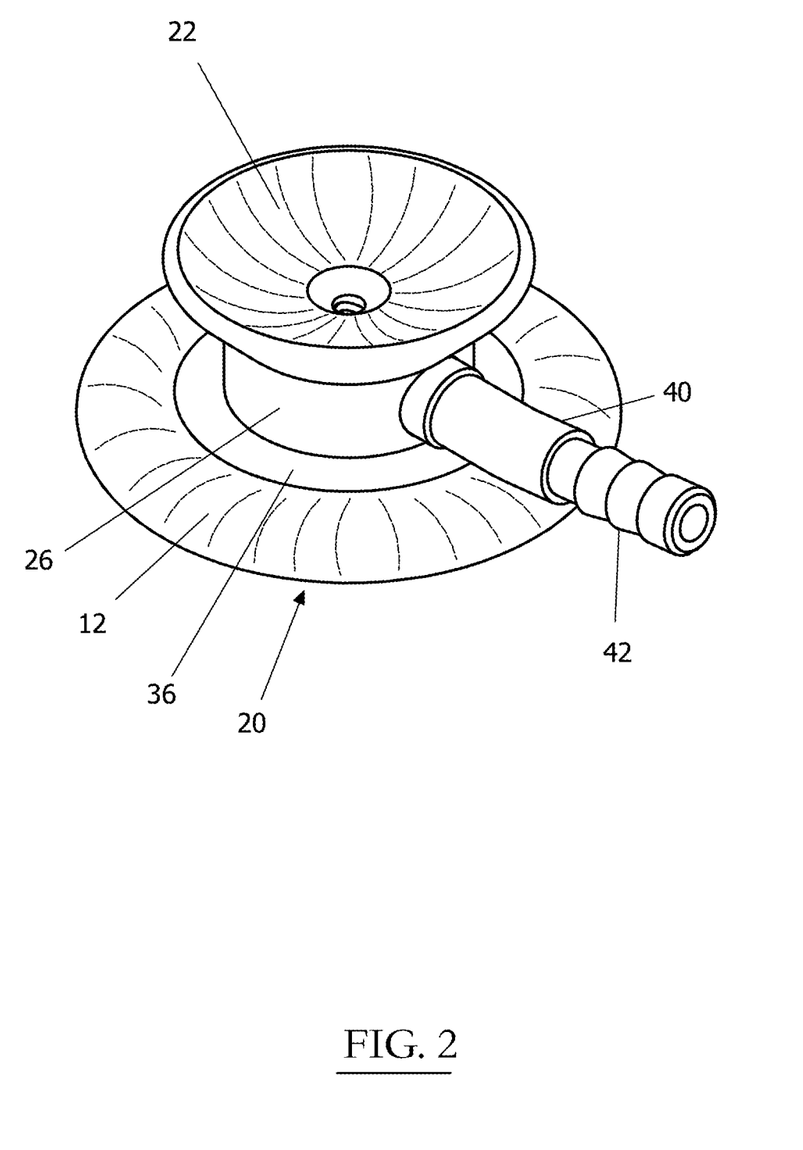
FIG. 2 is a perspective view of the stethoscope chestpiece of the stethoscope of FIG. 1.

Referring collectively to FIGS. 2 and 3, it can be seen that the rotatable acoustic valve 40 comprises a first end portion and a second end portion disposed opposite to the first end portion. The first end portion of the rotatable acoustic valve 40 is disposed within the chestpiece body portion 26 in the assembled state of the chestpiece 20, while the second end portion of the rotatable acoustic valve 40 has a barbed end portion 42 with a plurality of barbs for engaging an acoustic tube of the binaural assembly 28 (e.g., by elastically deforming the flexible acoustic tube 30).

With reference again to the transverse sectional view of FIG. 3, in the first operative position, the acoustic passageway portions 44, 46 of the rotatable acoustic valve 40 are fluidly coupled with the one-piece diaphragm and ring 12 via the lower acoustic passageway 38, while in the second operative position, the acoustic passageway portions 44, 46 of the rotatable acoustic valve 40 are fluidly coupled with the frustoconical bell portion 22 of the stethoscope chestpiece 20 via the upper acoustic passageway 24.

Next, referring to FIGS. 2-4, the one-piece diaphragm and ring 12 of the illustrative embodiment will be described in detail. In FIGS. 3 and 4, it can be seen that the diaphragm rim support portion 36 of the chestpiece 20 includes an annular projection 48 for accommodating the one-piece diaphragm and ring 12. As shown in the sectional view of FIG. 6, the one-piece diaphragm and ring 12 comprises a circumferential internal groove 15 that receives the annular projection 48 of the diaphragm rim support portion 36. As will be explained in more detail hereinafter, in the illustrative embodiment, the one-piece diaphragm and ring 12 is formed from a resilient material that elastically deforms when the circumferential internal groove 15 of the one-piece diaphragm and ring 12 is matingly engaged with the annular projection 48 of the diaphragm rim support portion 36.

Figure 5:
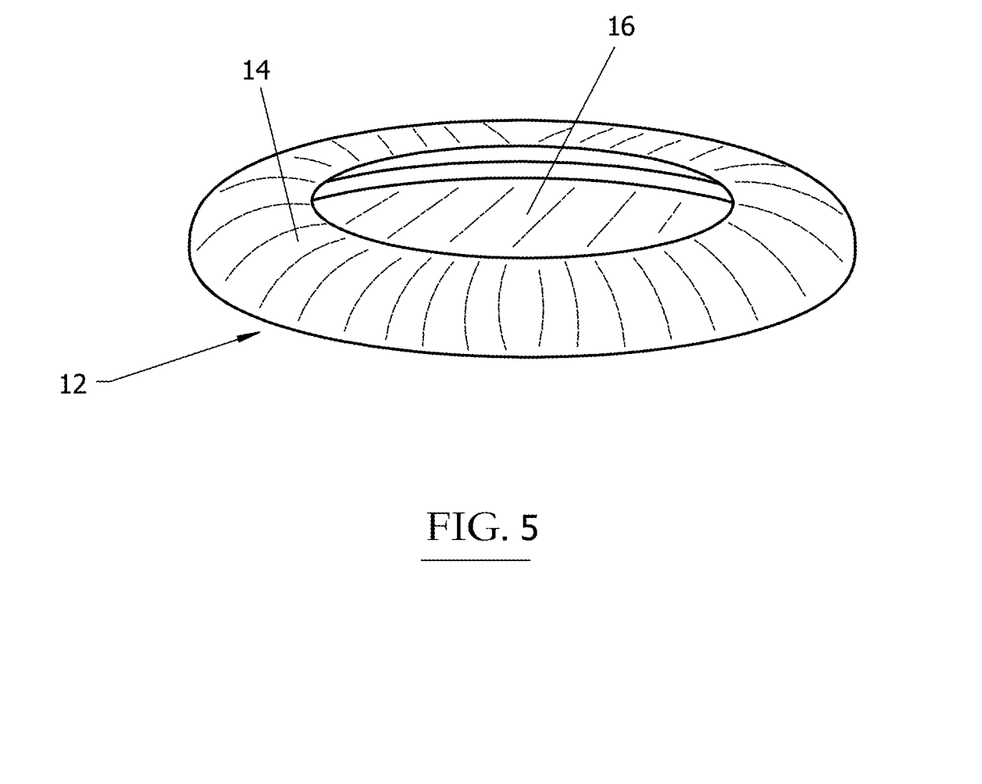
FIG. 5 is a perspective view of the one-piece diaphragm and ring of the stethoscope of FIG. 1.

The structural features of the illustrative embodiment of the one-piece diaphragm and ring 12 will be described with reference to FIGS. 5 and 6. As shown in these figures, the one-piece diaphragm and ring 12 comprises a diaphragm portion 16 having a flat disk shape; and a ring portion 14 connected to an outer periphery of the diaphragm portion 16. The ring portion 14 is integrally formed with the diaphragm portion 16. In the sectional view of FIG. 6, it can be seen that the internal recess profile of the ring portion 14 of the one-piece diaphragm and ring 12 corresponds to the external profile of the diaphragm rim support portion 36 of the chestpiece body portion 26. More particularly, the ring portion 14 of the one-piece diaphragm and ring 12 comprises the circumferential internal groove 15 just above the diaphragm portion 16, a vertical wall portion 17 extending upwardly from the circumferential internal groove 15, and an upwardly tapered portion 19 extending inwardly from the vertical wall portion 17 of the ring portion 14.

In the illustrative embodiment, the diaphragm portion 16 of the one-piece diaphragm and ring 12 has a thickness between approximately 0.27 millimeters and approximately 0.30 millimeters, inclusive, in an unstretched state prior to being installed on the chestpiece body portion 26 of the stethoscope chestpiece 20. Also, in the illustrative embodiment, the diaphragm portion 16 has a thickness between approximately 0.25 millimeters and approximately 0.28 millimeters, inclusive, in a stretched state after being installed on the chestpiece body portion 26 of the stethoscope chestpiece 20. In addition, with reference to FIG. 3, in the illustrative embodiment, the ring portion 14 is configured to overlap the diaphragm rim support portion 36 of the chestpiece body portion 26 by approximately 5 millimeters to 6 millimeters, inclusive, after being installed on the chestpiece body portion 26 of the stethoscope chestpiece 20. In FIG. 3, the overlap of the ring portion 14 relative to the diaphragm rim support portion 36 is denoted by the dimension line 18.

In the illustrative embodiment, the circumferential internal groove 15 of the ring portion 14 of the one-piece diaphragm and ring 12 has an inner diameter that is smaller than an outer diameter of the annular projection 48 of the chestpiece body portion 26 so that the diaphragm portion 16 of the one-piece diaphragm and ring 12 stretches when the one-piece diaphragm and ring 12 is attached to the chestpiece body portion 26. Advantageously, the stretching of the diaphragm portion 16 of the one-piece diaphragm and ring 12 when the one-piece diaphragm and ring 12 is installed on the chestpiece body portion 26 achieves greater surface tension in the diaphragm portion 16 so that the diaphragm portion 16 more effectively conducts sound in a manner similar to a musical drum.

Figure 6:
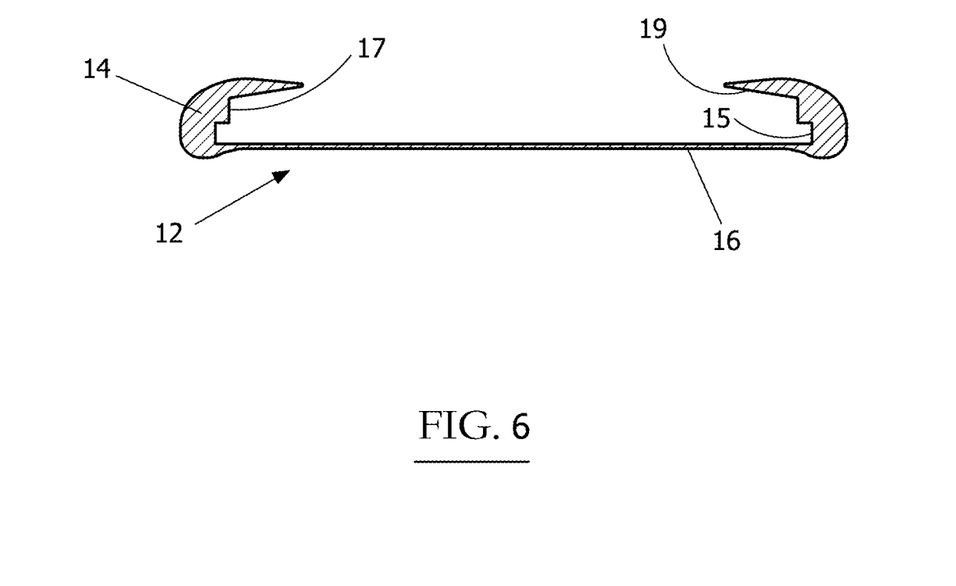
FIG. 6 is a cross-sectional view of the one-piece diaphragm and ring of FIG. 5, which is cut along a cutting-plane extending transversely through the center of the one-piece diaphragm and ring.

In the illustrative embodiment, as shown in FIGS. 3 and 6, a peripheral side of the ring portion 14 of the one-piece diaphragm and ring 12 has a thickness that is substantially greater than the remainder of the one-piece diaphragm and ring 12 so that the peripheral side of the ring portion 14 is capable of absorbing an impact without fracturing (i.e., the one-piece diaphragm and ring 12 will not crack like a conventional two-piece PVC diaphragm and ring). The thick peripheral side of the ring portion 14 acts as a bumper to absorb impacts when the chestpiece 20 contacts other objects.

In the illustrative embodiment, the one-piece diaphragm and ring 12 is formed from silicone. The silicone forming the one-piece diaphragm and ring 12 may have a density of approximately 1.15 grams per cubic centimeter. Also, the silicone forming the one-piece diaphragm and ring 12 may have an elasticity between approximately 7 megapascals and approximately 8 megapascals, inclusive. Advantageously, the silicone used to form the one-piece diaphragm and ring 12 is non-toxic and contains no plasticizers. Also, advantageously, the silicone used to form the one-piece diaphragm and ring 12 is odorless, age-resistant, heat-resistant, hardy, eco-friendly, difficult to discolor, and has a good softness.

In the illustrative embodiment, because the one-piece diaphragm and ring 12 is formed from a flexible material (i.e., silicone), the one-piece diaphragm and ring 12 is capable of conforming to one or more contours of a body portion of a patient (e.g., conforming to the chest curvature or the back curvature of the patient). Also, in the illustrative embodiment, the bottom side of the diaphragm portion 16, which contacts the body portion of the patient, has a matte surface so that the diaphragm portion 16 does not stick to the body portion of the patient.

Figure 7:
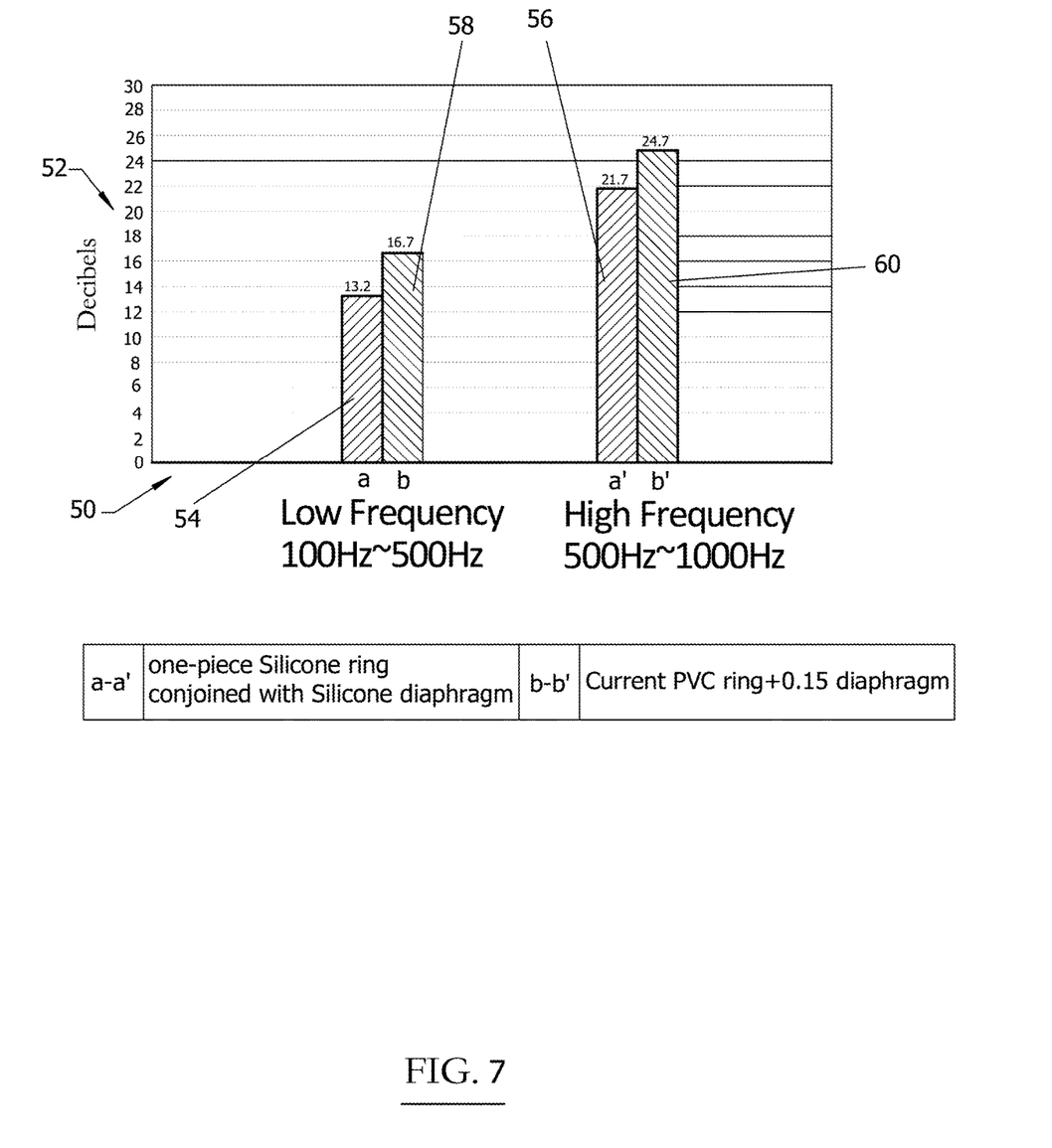
FIG. 7 is a graph depicting the high and low frequency characteristics of the one-piece diaphragm and ring as compared to a conventional two-part PVC ring and diaphragm.

The sound characteristics of the one-piece diaphragm and ring 12 of the illustrative embodiment will be described with reference to FIG. 7. In this figure, a graph 50 of diaphragm sound leakage test results is illustrated. In FIG. 7, the y-axis 52 of the graph 50 is the sound power loss measured in decibels. As shown in FIG. 7, for a low frequency range between 100 Hertz and 500 Hertz, the one-piece diaphragm and ring 12 formed from silicone has a sound power loss of 13.2 decibels (represented by bar 54 in graph 50), while a conventional separately formed polyvinyl chloride (PVC) ring and diaphragm has a sound power loss of 16.7 decibels (represented by bar 58 in graph 50). As such, in a low frequency range between 100 Hertz and 500 Hertz, the one-piece diaphragm and ring 12 results in a sound loss reduction of approximately 3.5 decibels as compared to the conventional two-piece diaphragm and ring formed from polyvinyl chloride (PVC). Referring again to FIG. 7, for a high frequency range between 500 Hertz and 1,000 Hertz, the one-piece diaphragm and ring 12 formed from silicone has a sound power loss of 21.7 decibels (represented by bar 56 in graph 50), while a conventional separately formed polyvinyl chloride (PVC) ring and diaphragm has a sound power loss of 24.7 decibels (represented by bar 60 in graph 50). Thus, in a high frequency range between 500 Hertz and 1,000 Hertz, the one-piece diaphragm and ring 12 results in a sound loss reduction of approximately 3.0 decibels as compared to the conventional two-piece diaphragm and ring formed from polyvinyl chloride (PVC). As such, the one-piece diaphragm and ring 12 advantageously results in a significant reduction in stethoscope sound loss. For example, in one or more embodiments, the one-piece diaphragm and ring 12 can result in an approximately 28% reduction in sound loss so that the stethoscope is able to output sounds that are approximately 5 decibels louder.

In one or more embodiments, the one-piece diaphragm and ring 12 is configured to be a single-use diaphragm and ring that is discarded after being used with a patient. Because the one-piece diaphragm and ring 12 is formed from a flexible material (e.g., silicone), the one-piece diaphragm and ring 12 is able to be quickly and easily removed from, and installed on the chestpiece body portion 26 so that the one-piece diaphragm and ring 12 is readily interchangeable (i.e., the one-piece diaphragm and ring 12 can be removed when contaminated with biological material and/or when the one-piece diaphragm and ring 12 needs replaced due to normal wear). Because the one-piece diaphragm and ring 12 overlaps more of the chestpiece body portion 26 than a conventional two-piece diaphragm and ring formed from polyvinyl chloride (PVC), the stethoscope 10 is more hygienic than a stethoscope using a conventional two-piece PVC diaphragm and ring because, in most cases, the only portion of the stethoscope 10 that touches the patient is the one-piece diaphragm and ring 12, and the one-piece diaphragm and ring 12 can be easily removed and replaced if it becomes contaminated. Also, because the one-piece diaphragm and ring 12 is made from a stretchable material, it can be securely attached to a myriad of different chestpiece body portions (i.e. the one-piece diaphragm and ring 12 can be used with many different manufacturers and models of stethoscope chestpieces).

Figure 8:
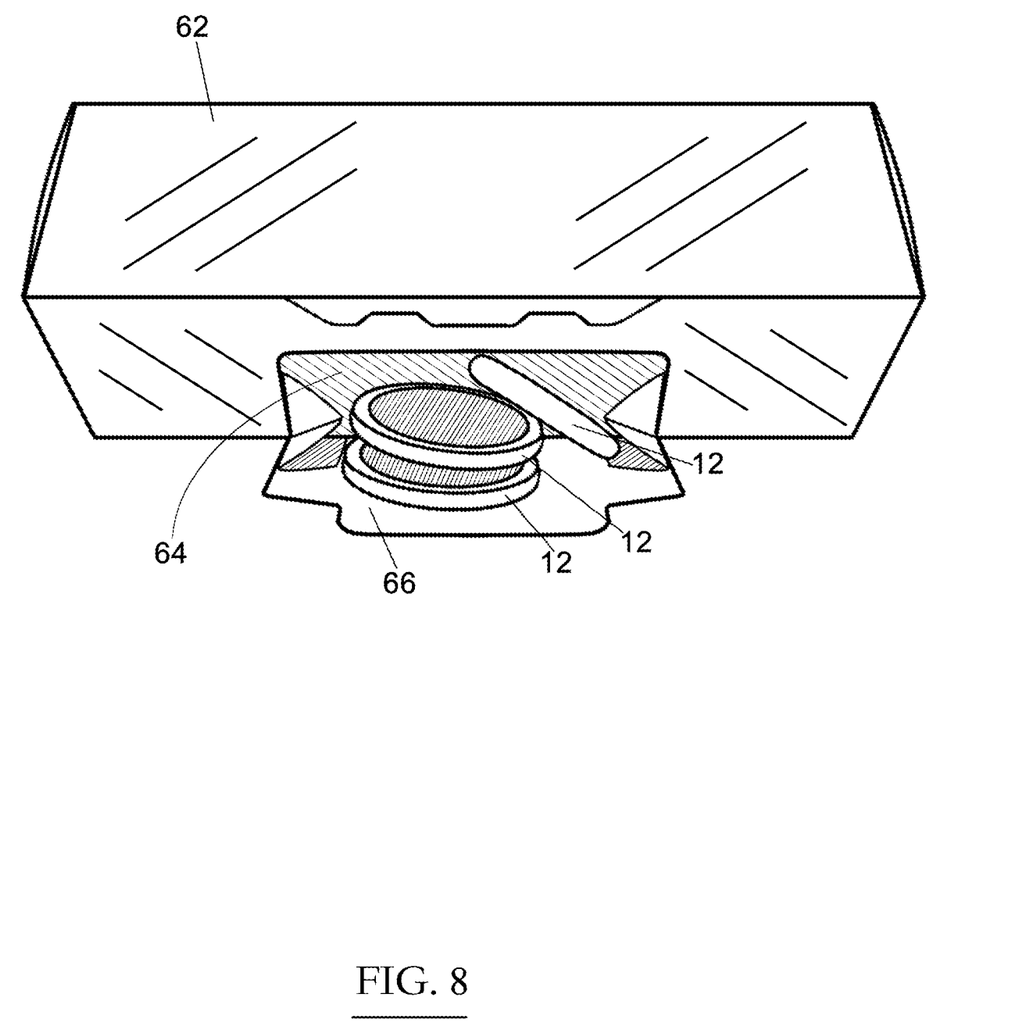
FIG. 8 is a perspective view of a dispenser box containing a plurality of stethoscope diaphragms, according to an illustrative embodiment of the invention.

Now, with reference to FIG. 8, an illustrative embodiment of a dispenser box 62 for a plurality of stethoscope diaphragms is depicted. In the illustrative embodiment, each of the stethoscope diaphragms 12 in the dispenser box 62 may comprise the one-piece diaphragm and ring 12 described above. As shown in FIG. 8, the dispenser box 62 comprises a dispensing opening 64 for allowing one or more stethoscope diaphragms 12 to be dispensed from the dispenser box 62. The dispensing opening 64 is created when the box flap 66 is opened by a user so as to allow the stethoscope diaphragms 12 to be dispensed from the dispenser box 62. As shown in FIG. 8, to facilitate the dispensing of the stethoscope diaphragms 12 from the dispenser box 62, in the open position of the box flap 66, the box flap 66 remains connected to the dispenser box 62 on its bottom edge and two side edges by means of opposed side wings. As such, the construction of the dispenser box 62 allows stethoscope diaphragms 12 to be hygienically dispensed therefrom.

In the illustrative embodiment, the dispenser box 62 may advantageously be configured to fit within a standard glove box holder so that single use stethoscope diaphragms can be easily dispensed alongside disposable exam gloves. As such, cross-contamination between patients can be prevented with the use of disposable stethoscope diaphragms 12 in the same manner that cross-contamination is prevented with disposable exam gloves. For example, in order to fit a standard glove box holder, the dimensions of the dispenser box 62 may have a width of approximately 5 inches (127 millimeters), a length of approximately 10 inches (254 millimeters), and a depth of approximately 3.75 inches (95 millimeters).

It is readily apparent that the aforedescribed one-piece diaphragm and ring 12 for a stethoscope chestpiece offers numerous advantages. First, the one-piece diaphragm and ring 12 for a stethoscope reduces sound leakage as compared to conventional stethoscope chestpieces with separate diaphragms and chill rings. Secondly, the one-piece diaphragm and ring 12 for a stethoscope is particularly useful for high frequency sounds. Finally, the one-piece diaphragm and ring 12 for a stethoscope is able to be formed from a polymeric material that is non-toxic, odorless, and pliable.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A one-piece diaphragm and ring for a stethoscope chestpiece, the one-piece diaphragm and ring comprising:
a diaphragm portion having a flat disk shape; and
a ring portion connected to an outer periphery of the diaphragm portion, the ring portion being integrally formed with the diaphragm portion, and the ring portion configured to be attached to a rim of a chestpiece body portion, the ring portion comprising a circumferential internal groove disposed therein, the circumferential internal groove of the ring portion configured to matingly engage with an annular projection of the chestpiece body portion, the ring portion further comprising a first vertical wall portion extending upwardly from the circumferential internal groove and a circumferential lip portion extending radially inward from the first vertical wall portion, and the circumferential internal groove being in a form of a circumferential cavity that extends radially outward from an edge of the first vertical wall portion to a second vertical wall portion that is radially spaced apart from the first vertical wall portion.

2. The one-piece diaphragm and ring according to claim 1, wherein the diaphragm portion and the ring portion are formed from silicone.

3. The one-piece diaphragm and ring according to claim 2, wherein the silicone forming the diaphragm portion and the ring portion has a density of approximately 1.15 grams per cubic centimeter.

4. The one-piece diaphragm and ring according to claim 2, wherein the silicone forming the diaphragm portion and the ring portion has an elasticity between approximately 7 megapascals and approximately 8 megapascals, inclusive.

5. The one-piece diaphragm and ring according to claim 2, wherein, in a low frequency range between 100 Hertz and 500 Hertz, the one-piece diaphragm and ring is configured to result in a sound loss reduction of approximately 3.5 decibels as compared to a conventional two-piece diaphragm and ring formed from polyvinyl chloride.

6. The one-piece diaphragm and ring according to claim 2, wherein, in a high frequency range between 500 Hertz and 1,000 Hertz, the one-piece diaphragm and ring is configured to result in a sound loss reduction of approximately 3.0 decibels as compared to a conventional two-piece diaphragm and ring formed from polyvinyl chloride.

7. The one-piece diaphragm and ring according to claim 1, wherein the diaphragm portion has a thickness between approximately 0.27 millimeters and approximately 0.30 millimeters, inclusive, in an unstretched state prior to being installed on the chestpiece body portion of the stethoscope chestpiece.

8. The one-piece diaphragm and ring according to claim 1, wherein the diaphragm portion has a thickness between approximately 0.25 millimeters and approximately 0.28 millimeters, inclusive, in a stretched state after being installed on the chestpiece body portion of the stethoscope chestpiece.

9. The one-piece diaphragm and ring according to claim 1, wherein the ring portion is configured to overlap the rim of the chestpiece body portion by approximately 5 millimeters to 6 millimeters, inclusive, after being installed on the chestpiece body portion of the stethoscope chestpiece.

10. A chestpiece of a stethoscope, comprising:
a chestpiece body portion having a first end and a second end, the second end being oppositely disposed with respect to the first end, the second end of the chestpiece body portion having a rim, and the chestpiece body portion comprising an annular projection extending outwardly from a peripheral side thereof; and
a one-piece diaphragm and ring attached to the chestpiece body portion, the one-piece diaphragm and ring including:
a diaphragm portion having a flat disk shape; and
a ring portion connected to an outer periphery of the diaphragm portion, the ring portion being integrally formed with the diaphragm portion, and the ring portion attached to the rim at the second end of the chestpiece body portion, the ring portion comprising a circumferential internal groove disposed therein, the circumferential internal groove of the ring portion configured to matingly engage with the annular projection of the chestpiece body portion, the ring portion further comprising a first vertical wall portion extending upwardly from the circumferential internal groove and a circumferential lip portion extending radially inward from the first vertical wall portion, and the circumferential internal groove being in a form of a circumferential cavity that extends radially outward from an edge of the first vertical wall portion to a second vertical wall portion that is radially spaced apart from the first vertical wall portion.

11. The chestpiece of a stethoscope according to claim 10, wherein the circumferential internal groove of the ring portion of the one-piece diaphragm and ring has an inner diameter that is smaller than an outer diameter of the annular projection of the chestpiece body portion so that the diaphragm portion of the one-piece diaphragm and ring stretches when the one-piece diaphragm and ring is attached to the chestpiece body portion.

12. The chestpiece of a stethoscope according to claim 10, wherein the diaphragm portion and the ring portion of the one-piece diaphragm and ring are formed from silicone.

13. The chestpiece of a stethoscope according to claim 12, wherein the silicone forming the diaphragm portion and the ring portion has a density of approximately 1.15 grams per cubic centimeter.

14. The chestpiece of a stethoscope according to claim 12, wherein the silicone forming the diaphragm portion and the ring portion has an elasticity between approximately 7 megapascals and approximately 8 megapascals, inclusive.

15. The chestpiece of a stethoscope according to claim 12, wherein, in a low frequency range between 100 Hertz and 500 Hertz, the one-piece diaphragm and ring is configured to result in a sound loss reduction of approximately 3.5 decibels as compared to a conventional two-piece diaphragm and ring formed from polyvinyl chloride.

16. The chestpiece of a stethoscope according to claim 12, wherein, in a high frequency range between 500 Hertz and 1,000 Hertz, the one-piece diaphragm and ring is configured to result in a sound loss reduction of approximately 3.0 decibels as compared to a conventional two-piece diaphragm and ring formed from polyvinyl chloride.

17. The chestpiece of a stethoscope according to claim 10, wherein the diaphragm portion of the one-piece diaphragm and ring has a thickness between approximately 0.27 millimeters and approximately 0.30 millimeters, inclusive, in an unstretched state prior to being installed on the chestpiece body portion of the stethoscope chestpiece.

18. The chestpiece of a stethoscope according to claim 10, wherein the diaphragm portion of the one-piece diaphragm and ring has a thickness between approximately 0.25 millimeters and approximately 0.28 millimeters, inclusive, in a stretched state after being installed on the chestpiece body portion of the stethoscope chestpiece.

19. The chestpiece of a stethoscope according to claim 10, wherein the ring portion of the one-piece diaphragm and ring is configured to overlap the rim of the chestpiece body portion by approximately 5 millimeters to 6 millimeters, inclusive.

20. The chestpiece of a stethoscope according to claim 10, wherein the one-piece diaphragm and ring is configured to be a single-use diaphragm and ring that is discarded after being used with a patient.

21. The chestpiece of a stethoscope according to claim 10, wherein a peripheral side of the ring portion of the one-piece diaphragm and ring has a thickness that is substantially greater than the remainder of the one-piece diaphragm and ring so that the peripheral side of the ring portion is capable of absorbing an impact without fracturing.

22. The chestpiece of a stethoscope according to claim 10, wherein the diaphragm portion and the ring portion of the one-piece diaphragm and ring are formed from a flexible material so that the one-piece diaphragm and ring is capable of conforming to one or more contours of a body portion of a patient.

23. The chestpiece of a stethoscope according to claim 10, wherein the diaphragm portion and the ring portion of the one-piece diaphragm and ring are formed from a flexible material that enables the one-piece diaphragm and ring to be quickly and easily removed from, and installed on the chestpiece body portion so that the one-piece diaphragm and ring is readily interchangeable.

24. A one-piece diaphragm and ring for a stethoscope chestpiece, the one-piece diaphragm and ring comprising:
a diaphragm portion having a flat disk shape; and
a ring portion connected to an outer periphery of the diaphragm portion, the ring portion being integrally formed with the diaphragm portion, and the ring portion configured to be attached to a rim of a chestpiece body portion;
wherein the diaphragm portion and the ring portion are formed from silicone, the silicone forming the diaphragm portion and the ring portion has a density of approximately 1.15 grams per cubic centimeter; and the silicone forming the diaphragm portion and the ring portion has an elasticity between approximately 7 megapascals and approximately 8 megapascals, inclusive.

* * * * *